United States Patent
Narayanan et al.

(10) Patent No.: US 6,541,516 B1
(45) Date of Patent: Apr. 1, 2003

(54) WATER MISCIBLE EMULSIONS OF PYRETHROID INSECTICIDES OR TRIAZOLE FUNGICIDES

(75) Inventors: Kolazi S. Narayanan, Wayne, NJ (US); Domingo I. Jon, New York, NY (US)

(73) Assignee: ISP Investments Inc., Wilmington, DE (US)

( * ) Notice: Subject to any disclaimer, the term of this patent is extended or adjusted under 35 U.S.C. 154(b) by 0 days.

(21) Appl. No.: 09/952,120

(22) Filed: Sep. 14, 2001

(51) Int. Cl.[7] .................................................. A01N 53/00
(52) U.S. Cl. ........................ 514/531; 424/405; 504/101; 504/212; 504/272; 514/521
(58) Field of Search .................................. 514/531, 241, 514/521, 65, 383; 424/405; 504/101, 212, 227, 272

(56) References Cited

U.S. PATENT DOCUMENTS 5,156,666 A * 10/1992 Narayanan et al. ............. 71/79
5,435,939 A * 7/1995 Narayanan .................. 252/312

* cited by examiner

*Primary Examiner*—Neil S. Levy
(74) *Attorney, Agent, or Firm*—Walter Katz; William J. Davis; Marilyn J. Maue

(57) ABSTRACT

Clear, high load water miscible emulsions of pyrethroid insecticides or triazole fungicides, as a single phase, translocatable composition which is free of xylene and alkylphenol ethoxylate surfactants and concentrate matrix for the active agricultural component at between about 5 and about 25 wt. % active concentration.

9 Claims, No Drawings

WATER MISCIBLE EMULSIONS OF PYRETHROID INSECTICIDES OR TRIAZOLE FUNGICIDES

BACKGROUND OF THE INVENTION

Agriculturally active chemicals are most preferably applied in the form of aqueous emulsions, solutions or suspensions. Occasionally, they may also be applied in the form of a dust wherein the active ingredient is adsorbed onto or mixed with a finely divided inert carrier material, such as, china clay, or the like. With such powdered or dust compositions, drift due to wind is a problem and consequently, liquid formulations are preferred.

One of the problems with such liquid formulations is the fact that chemicals possessing agricultural activity, particularly those high load active concentrations, often exhibit extreme insolubility in water. This results in their having to be dissolved either in organic solvents or utilized in the form of emulsions subsequent to phase separation or suspensions. With respect to the use of organic solvents, such as xylene, or phenolic esters, these are generally disadvantageous from an environmental and cost viewpoint. Particularly, such organic chemicals may exhibit toxicity or side-effects which may be adverse to the effect of the agricultural chemical itself or to the subsequent fruit or vegetable produced in the particular agricultural use. This toxicity may also be disadvantageous with respect to inhalation during handling and flammability.

When attempts are made to provide emulsified or suspension formulations, difficulties are encountered with respect to providing a desirably high concentration of the agriculturally active ingredient. Thus, when such agriculturally active chemicals are formulated into a macroemulsion (sometimes referred to herein as an emulsion), it is difficult to maintain the emulsified state. This, in turn, creates problems in maintaining a uniform formulation and subsequent plant dosage, particularly, when the formulation is diluted with water for application on the plants.

U.S. Pat. No. 5,317,042 disclosed a clear stable, efficacious aqueous microemulsion of an agriculturally active chemical, alone, or in a complex mixture, obtained by incorporating the chemical in an inert matrix composition containing a defined mixture of nonionic surfactant to form a microemulsion concentrate which is subsequently diluted with water for plant treatment. Patentee's inert matrix composition consists of a predetermined mixture of nonionic surfactants which include nonylphenol ethoxylate having an HLB of >6. However, the presence of nonylphenol ethoxylate in the formulation is considered detrimental from an ecological standpoint.

U.S. Pat. No. 6,187,715 described water-based microemulsions of a lower alkyl ester of quinoxalinyl herbicide including 20 to 50 wt. % of a heavy aromatic petroleum distillate.

Accordingly, it is an object of this invention to provide a substantially stable homogeneous, water soluble microemulsion containing at least 5 wt. % of an active pyrethroid insecticide or a triazole fungicide which is free of toxic and environmentally objectionable surfactants.

Another object is to provide a stable concentrate containing such actives in high load which is readily soluble in water and suitable for spraying crops.

These and other benefits and objectives will become apparent from the following description and disclosure.

SUMMARY OF THE INVENTION

In accordance with the present invention there is provided a stable, liquid homogeneous concentrate matrix comprising MICROFLEX® admixed with a hydrophobic oil, preferably a heavy aromatic petroleum oil distillate boiling between 100° F. and 250° F., combined in a weight ratio of between about 4.5–50:1 MICROFLEX® to oil, which corresponds to about 2–18 wt. % of oil therein.

Within these ranges, preferably 5–15%, and, most preferably 2–12%, the actives dissolve readily in the concentrate and stable, homogeneous compositions are obtained upon dilution with water for spraying. The present concentrate thus can be diluted with up to 99.9 wt. % water to provide a homogeneous liquid spray for treating plants.

The general formula for the MICROFLEX® composition is described in the SUMMARY OF THE INVENTION, elements (b) through (f) in U.S. Pat. No. 6,045,816. The teaching of this patent is incorporated herein by reference.

The above matrix concentrate is capable of loading up to 25 wt. % of an active pyrethroid insecticide or triazole fungicide. A pyrethroid is a class of well known and widely-used insecticides of which cypermethrin, D-allethrin, permethrin, piperonyl butoxide and tetramethrin are representative examples.

Other agricultural active chemicals which may be included in the compositions of the invention are: permethrin; permethrin+Kathon®, D-allethrin; tetramethrin; deltamethrin; piperonyl butoxide; mixed pyrethroids; dicofol; tefluthrin; resmethrin; phenothrin; kadethrin; bifenthrin; cyhalothrin; cycloprothrin; tralomethrin; cyfluthrin; fenvalerate and isomers; fenpropathrin; fluvalenate; rotenone; biphenyl compounds like, methoxychlor; chlorbenzilate; bromopropylate and chlorfenethol.

DETAILED DESCRIPTION OF THE INVENTION

The basic concentrate of this invention comprises a mixture of MICROFLEX® and a hydrophobic oil such as heavy aromatic petroleum oil distillate. To achieve a clear, homogeneous composition upon dilution, the ratio of oil should be 4.5 to 50:1. More desirably a weight % of oil of 5–15% oil is employed to obtain a homogeneous sprayable solution.

The oil distillates suitably employed for the present MICROFLEX® mixture have an average boiling point of between 100° and 250° F. and are commercially available as fractions from crude oil distillation. Typical of such oils are Exxon 200, Aromatic 150, Aromatic 200 available from Exxon and Texaco 400. Generally these oil fractions contain a major portion of aromatic solvent naphtha and a minor portion of middle distillate solvent extract of which about a 55–65/35–45 mixture is most desirable. Normally these oils, which contain predominantly aromatics, are compounds having 8 to 15 carbon atoms and primarily 10–12 carbon atoms. The flash point of these distillates is preferably above 200° F.

As indicated above the MICROFLEX® composition of this invention is a mixture and contains (i) 0 to about 60 wt. %, preferably 0.15 to 40 wt. %, of a N—$C_1$ to $C_4$ alkyl lactam such as an N-alkyl pyrrolidone, an N-alkyl caprolactam or mixtures thereof;

(ii) from about 0.002 to about 40 wt. %, preferably 0.05 to 29 wt. % of a N—$C_8$ to $C_{18}$ alkyl lactam such as an N-alkyl pyrrolidone, an N-alkyl caprolactam and mixtures thereof, (iii) 0 to abut 30 wt. %, preferably 0.5 to 15 wt. %, of an ethylene oxide/propylene oxide block copolymer surfactant;

(iv) 0.03 to about 80 wt. %, preferably 40 to 70 wt. %, of an alkoxylated castor oil, tristyryl phenol ethoxylate or a mixture thereof and (v) 0 to about 10 wt. %, preferably 0.005 to 6 wt. % of a phosphate ester buffer.

In the above MICROFLEX® composition, N-methyl- and N-octyl-lactams, particularly N-methyl- and N-octyl-pyrrolidones, are preferred. Although the above lactams can be ring substituted with $C_1$ to $C_4$ alkyl radicals, unsubstituted species are more desirable.

In general, the present concentrate containing the active component is prepared by initially combining MICROFLEX® as an anhydrous mixture with the oil fraction and then gradually adding between about 5 to about 25% by weight of the active component. This operation can be carried out under continuous agitation over a period of from about 0.5 to about 6 hours at ambient temperature up to a temperature below the boiling point of the oil. The resulting mixture is a substantially clear, somewhat viscous liquid which can be diluted with up to 99.9 wt. % of water to form a stable microemulsion suitable for treating a plant area. The concentrate when diluted with either soft or (100–1000 ppm) hard water is stable at both low and high temperatures over the two-week period tested. The concentration of the active component in the diluted concentrate can vary widely depending on the dosages conventionally recommended, the type of plant to be treated, the atmospheric conditions encountered in field spraying etc. Usually an active concentration of between about 0.01 and about 5 wt. %, more often, between about 0.1 and about 1.5 wt. %, is sufficient to exert an insecticidal or fungicidal affect. Because of the present matrix, the admixed agrochemical possesses superior translocation capability both in the xylem and in the phloem of the plant and can be applied at any stage of plant development. The emulsion is also effective in preventing seed maturation and therefore possesses both pre-emergent and post emergent properties.

The concentrates of this invention, containing or omitting the active component, can be supplied to the consumer for on-site formulation which may or may not include the dilution with water and/or the addition of one or more active agents.

Inert excipients can be added to the concentrate or to the diluted concentrate when desired. Accordingly, such additives as a wetting agent, e.g. a dialkyl polysiloxane, a cosolvent, e.g. cyclohexanone, octanol, and other polar solvents and/or a spreading and sticking agent, e.g. phthalic glycerol, an alkyd resin and the like can be incorporated in these compositions. When employed, these excipients generally may comprise between about 0.05 and about 5 wt. % of the total diluted composition.

Preparation of MICROFLEX®

Several batches of MICROFLEX® were each prepared by mixing 21.3 g of N-methyl pyrrolidone (NMP), 9.3 g of N-octyl pyrrolidone, 9.3 g of EO/PO block copolymer surfactant (PLURONIC L-31*), 56 g of ethoxylated castor oil with 30 EO (Alkamuls EL 620) and 4 g of ethoxylated phosphate ester with 9.7 EO (Rhodafac RS 710). 5–15 g of pyrethroids (cypermethrin, cyfluthrin or prallethrin as shown below) were dissolved in a 95–85 g of premixed samples of MICROFLEX® AND VARYING AMOUNTS OF AROMATIC OIL (Exxon aromatic 200), labeled Samples A through C. Each of the samples was mixed at ambient temperature over a period of 3 hours. The results of these tests are reported in Examples 1–3 below.

* supplied by BASF
** supplied by Rhodia

EXAMPLE 1

Physical stability upon dilution of composition of MICROFLEX® with 7 wt. % of Aromatic 200, "A", and Ag Actives, %

| A | 85 |
|---|---|
| Cypermethrin | 12.0 |
| Cyfluthrin | 1.5 |
| Prallethrin | 1.5 |
| Total | 100 |

Diluted to 1/100, 1/500, 1/1000.
Clear homogeneous composition with stability after dilution. No separation for a period of one week.

EXAMPLE 2

A "B" MICROFLEX® composition was prepared as above with 10 wt. % aromatic oil.

| B | 85 |
|---|---|
| Cypermethrin | 12 |
| Cyfluthrin | 3 |
| Total | 100 |

Diluted to 1/100, 1/500, 1/1000. No separation for one week.

EXAMPLE 3

A "C" MICROFLEX® composition was prepared with 15 wt. % aromatic oil.

| C | 95 |
|---|---|
| Cyfluthrin | 5 |
| Total | 100 |

Dilution 1/10, 1/100, 1/500, 1/1000 with 1000 ppm hard water. No separation for one week at room temperature.

COMPARATIVE TESTS

Similar compositions, with <2 wt. %, or >18% Aromatic 200, upon dilution in water, were unstable after <1 day, or caused extreme difficulty in dissolving the actives, respectively.

<2% aromatic 200 is not enough to produce enhanced stability after dilution. >18% aromatic 200 caused difficulty in dissolving the actives.

What is claimed is:

1. A concentrate of a liquid, water miscible matrix for an agrochemically active compound consisting essentially of from 5 to 25 wt. % of the agrochemical wherein the agrochemical is a pyrethroid or a triazole fungicide; 75–95 wt. % of the following: a mixture of one part of a heavy aromatic petroleum distillate boiling above 100° F. and between 4.5 to 50 parts of a mixture comprising by weight (i) 0 to 60% of a N—$C_1$ to $C_4$ alkyl lactam, (ii) 0.002 to 40% of a $C_8$ to $C_{18}$ alkyl lactam, (iii) 0 to 30% of an ethylene oxide/propylene oxide block copolymer, (iv) 0.03 to 80% of an alkylated castor oil, tristyryl phenol ethoxylate or a mixture thereof and (v) 0 to 10% of a phosphate ester buffer.

2. The concentrate of claim 1 containing between by weight (i) 0.15–40%, (ii) 0.05–29%, (iii) 0.5–15%, (iv) 40–70% and (v) 0.005–6%.

3. A stable, homogeneous water composition comprising the concentrate of one of claims 1 or 2 having between 0.05 to 2.5 wt. % of said active agrochemical based on total composition.

4. The composition of claim 3 wherein the active is a pyrethroid insecticide.

5. The composition of one of claims 1 or 4 wherein said active agrochemical is a pyrethroid insecticide.

6. A concentrate according to claim 1 wherein the distillate is present in an amount of about 5–15 wt. % of the concentrate.

7. A stable, homogeneous water microemulsion composition comprising the concentrate of one of claims 1 or 2 which is diluted with up to 99.9 wt. % of water.

8. A concentrate comprising a liquid, water soluble matrix containing from 5 to 25 wt. % of an agrochemically active compound selected from the group consisting of a pyrethroid insecticide and a triazole fungicide, and 75–95 wt. % of a matrix mixture of 1 part of an aromatic petroleum distillate boiling above 100° F. and between 4.5 to 50 parts of a mixture comprising (i) 0 to 60% of a N—C to $C_4$ alkyl lactam, (ii) 0.002 to 40% of a $C_8$ to $C_{18}$ alkyl lactam, (iii) 0 to 30% of an ethylene oxide/propylene oxide block copolymer, (iv) 0.03 to 80% of an alkylated castor oil, tristyryl phenol ethoxylate or a mixture thereof, and (v) 0 to 10% of a phosphate ester buffer, and additionally containing 1–60 wt. % of one or more emulsifiers, based on said mixture.

9. A concentrate according to claim 8 wherein said wt. ratio of distillate to mixture is one part of distillate to 5–15 parts of said mixture.

* * * * *